(12) United States Patent
Seelig

(10) Patent No.: US 9,534,254 B1
(45) Date of Patent: Jan. 3, 2017

(54) PATIENT STRATIFICATION FOR CANCER THERAPY BASED ON GENOMIC DNA MICROARRAY ANALYSIS

(75) Inventor: Steven A. Seelig, Naperville, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 0 days.

(21) Appl. No.: 09/539,400

(22) Filed: Mar. 31, 2000

Related U.S. Application Data

(63) Continuation-in-part of application No. 09/243,067, filed on Feb. 2, 1999, now Pat. No. 6,251,601.

(51) Int. Cl.
*C12Q 1/68* (2006.01)

(52) U.S. Cl.
CPC ........... *C12Q 1/6886* (2013.01); *C12Q 1/6841* (2013.01)

(58) Field of Classification Search
USPC .... 435/6, 69.1, 320.1; 536/26.6; 422/50, 52, 422/55, 56, 57, 68.1
See application file for complete search history.

(56) References Cited

U.S. PATENT DOCUMENTS

| | | | |
|---|---|---|---|
| 5,807,522 A | 9/1998 | Brown et al. | |
| 5,972,606 A | 10/1999 | Creasy et al. | |
| 6,004,755 A | 12/1999 | Wang | |
| 6,165,709 A * | 12/2000 | Friend et al. | 435/4 |
| 6,251,601 B1 | 6/2001 | Bao et al. | |
| 6,544,735 B1 * | 4/2003 | Williamson | 506/9 |

OTHER PUBLICATIONS

Cronin et al. (1996, Human Mutation, p. 244-255).*
Berns et al. (Gene, 1995, vol. 159, p. 11-18).*
Courjal et al. (Cancer Res, 1997, 57:4368-4377).*
Osin et al. (Adjuvant Therapy of Primary Breast Cancer; 1998, p. 35-48).*
Clark et al. (Breast Cancer, 1995, 2(2):79-89).*
Pinkel et al. (Nature Genetics, 1998, p. 207-211).*

* cited by examiner

*Primary Examiner* — Stephanie K Mummert
(74) *Attorney, Agent, or Firm* — Lisa V. Mueller; Michael Best & Friedrich LLP

(57) ABSTRACT

The method of the invention comprises the stratification of a cancer patient population into various cancer therapy groups based on analysis by genomic DNA microarray of multiple gene amplifications or deletions present or absent in the diseased tissue of each patient. In particular, the invention involves patient stratification into one of at least four cancer therapy groups based on the microarray analysis of gene amplification or gene deletion at multiple chromosome locations.

21 Claims, 2 Drawing Sheets

MICROARRAY CHIP

PROBE CLIP

TOP VIEW

CHIP HOLDER – TOP VIEW

SIDE VIEW

CHIP HOLDER – SIDE VIEW

HYBRIDIZATION CARTRIDGE

PATIENT STRATIFICATION FOR CANCER THERAPY BASED ON GENOMIC DNA MICROARRAY ANALYSIS

RELATED APPLICATION

This application is a continuation-in-part of commonly Assigned U.S. patent application Ser. No. 09/243,067, filed 2 Feb. 1999, "Simultaneous Measurement of Gene Expression and Genomic Abnormalities Using Nucleic Acid Microarrays, Y. Bao, et al, now U.S. Pat. No. 6,251,601 B1".

FIELD OF THE INVENTION

This invention relates generally to the use of nucleic acid probe test to guide therapeutic selection for the treatment of cancer. More particularly, the invention relates to the stratification of a human cancer patient population into various cancer therapy groups based on the use of a genomic deoxyribonucleic acid ("DNA") microarray to assess a tissue sample from the patient.

BACKGROUND OF THE INVENTION

Abnormalities in the expression of genes, both in the timing and level of expression of particular genes, are a fundamental cause of cancer and other human disease. Abnormalities in genomic DNA, i.e. in chromosomes, are also a fundamental cause of cancer and other human disease, often leading to the over-expression or under-expression of genes. Some chromosomal abnormalities, such as balanced translocations and inversions between chromosomes, and base pair changes, do not involve a change in DNA sequence copy number. Other genomic DNA abnormalities comprise changes in DNA sequence copy number from the normal two copies per cell. These genomic DNA abnormalities often are referred to as gene amplification for copy number increase and gene deletion for copy number decrease. For example, one aggressive form of breast cancer, occurring in about 25-30% of breast cancers, results from the gene amplification and over-expression of the Her-2/neu oncogene, which is located on chromosome 17 at band q12. Breast cancer patients with this genetic abnormality have a significantly poorer prognosis, both for overall survival and disease-free survival, then patients without this abnormality. Proper assessment and management of breast cancer thus requires tests to measure the presence of Her-2 gene chromosomal copy number.

Chromosomal abnormalities such as Her-2 gene copy number can be assessed by assays using fluorescent in situ hybridization ("FISH"). FISH assays involve hybridization of DNA probes to chromosomal DNA present in morphologically intact metaphase spreads or interphase cells of tissue samples. The U.S. Food and Drug Administration recently approved a diagnostic FISH test, PathVysion™ HER-2, available from Vysis, Inc. (Downers Grove, Ill.) for detection of HER-2 copy number and prediction of outcome of anthracyclin therapy in node positive breast cancer patients.

Cancer also involves abnormalities in multiple genes, leading to multiple forms of the disease, as exemplified by breast cancer, wherein the Her-2 oncogene is not abnormal in the majority of cases. So-called "DNA Chip" or "microarray" tests using hybridization to a two dimensional array of multiple nucleic acid probes attached to a solid substrate assess multiple gene expression abnormalities simultaneously. See for example, U.S. Pat. No. 5,445,934, "Array of Oligonucleotides on Solid Substrate," Fodor, et al., U.S. Pat. No. 5,800,992, "Method of Detecting Nucleic Acids," Fodor, et al., and U.S. Pat. No. 5,807,552, "Methods for Fabricating Microarrays of Biological Substances," Brown, et al. The microarray gene expression tests are of growing use in the development of new drugs targeted at particular diseases.

Multiple gene expression at the protein level also can be examined by the use of "microdot" immunoassays, which are two dimensional arrays of immobilized antigens on a substrate. See U.S. Pat. No. 5,486,452, "Devices and Kits for Immunological Analysis," Gordon, et al., priority date Feb. 3, 1982, and Ekins, et al, *Analytica Chimica Acta*, 227:73-96 (1989). The immobilized antigens of Gordon, et al. include nucleic acids and are disclosed as arrayed at densities of $10^5$ per 10 square centimeters (or 1,000 per $cm^2$). Gordon, et al. further disclose the array has "intrinsic resolution" below the size of pipetting devices common in 1982, see Gordon, et al. at column 17, and can thus contain antigens at higher densities. Gordon, et al. disclose that the arrays can be manufactured by use of mechanical transfer apparatus, miniaturized applicators, lithographic procedures or high speed electronic printing.

U.S. Pat. No. 5,665,549, "Comparative Genomic Hybridization (CGH)," Pinkel, et al., discloses a method for simultaneous assessment of multiple genetic abnormalities. CGH involves the comparative, multi-color hybridization of a reference nucleic acid population labeled in one fluorescent color and a sample nucleic acid population labeled in a second fluorescent color to all or part of a reference genome, such as a human metaphase chromosome spread. Comparison of the resulting fluorescence intensity at locations in the reference genome permits determination of copy number of chromosomal sequences, or of expressed gene sequences, in the sample population. Microarray-based CGH tests have also been disclosed for the assessment of multiple genomic DNA or gene expression abnormalities, see U.S. Pat. No. 5,830,645, "Comparative Fluorescent Hybridization to Nucleic Acid Arrays, Pinkel, et al.; co-pending and commonly assigned U.S. patent application Ser. No. 09/085,625, "Improvements of Biological Assays for Analyte Detection," Muller, et al.; and Pinkel, et al., "High resolution analysis of DNA copy number variation using comparative genomic hybridization to microarrays," *Nature Genetics*, Vol. 20, October 1998, pp. 207-211. Pinkel, et al. in *Nature Genetics* disclose the capability of CGH to a microarray target to detect a single copy change in genomic DNA.

The PathVysion HER-2 FISH assay was the first in vitro diagnostic test approved by the FDA for clinical use to predict cancer therapeutic outcome based upon a nucleic acid probe test of patient tissue. In its approved clinical use, the PathVysion assay allows the stratification of node positive breast cancer patients into two groups: (i) HER-2 amplified and likely to respond to high dose anthracyclin therapy and (ii) HER-2 non-amplified and unlikely to need high dose anthracyclin therapy. This classification is highly significant because use of high dose anthracyclin therapy entails a higher risk of cardiotoxicity than lower dosage. What is needed for clinical cancer management are additional in vitro diagnostic tests such as the PathVysion assay that will allow the clinician to further refine cancer therapy selection for a particular patient.

It is an object of this invention to stratify cancer patients into various cancer therapy groups based on analysis of disease tissue using a genomic DNA microarray for multiple gene amplifications or deletions present or absent in the diseased tissue of the patient. It is another object to stratify a particular patient into one of at least four different cancer therapy groups based on the microarray analysis of gene amplification or gene deletion at multiple chromosome locations. It is a further object to stratify a particular patient into one of at least nine different cancer therapy groups based on the microarray analysis. Other objects of the invention will be detailed below.

SUMMARY OF THE INVENTION

The method of the invention comprises the stratification of a cancer patient population into various cancer therapy groups based on analysis by a nucleic acid microarray of multiple gene amplifications or deletions present or absent in the chromosomal DNA of the diseased tissue of each patient. In particular, the invention involves patient stratification into at least four cancer therapy groups based on the microarray analysis of gene amplification or gene deletion at multiple chromosome locations. The invention thus comprises a method of cancer patient stratification into one of at least four cancer therapy groups comprising:

(a) providing a diseased tissue or suspected disease tissue sample from a patient;

(b) extracting chromosomal DNA from the tissue sample to produce a chromosomal DNA sample;

(c) testing the chromosomal DNA sample by hybridizing the chromosomal DNA sample under hybridization conditions to a nucleic acid microarray to detect in the chromosomal DNA of the tissue sample a sufficient number of gene amplifications or gene deletions to permit patient stratification into one of at least four cancer therapy groups; and (d) stratifying the patient into one of at least four cancer therapy groups based on presence or absence of at least one of the gene amplifications or gene deletions.

The methods of the invention employ hybridization under suitable hybridization conditions of a genomic chromosomal DNA sample derived from a patient tissue sample to a nucleic acid microarray comprising multiple nucleic acid target elements attached to a solid support. A genomic chromosomal DNA sample generally contains both one or more "exon" sequences, which code for all or part of an RNA expressed gene sequence, and one or more "intron," non-coding sequences, which also often contain repeat sequences replicated at many points in the human genome. By hybridization of the genomic chromosomal DNA sample extract from the patient tissue to a microarray with nucleic acid target elements complementary to multiple nucleic acid gene sequences, the gene amplification or gene status for genes corresponding to the nucleic acid target elements can be assessed. The array format used in the methods of the invention comprises a microarray of separate nucleic acid target elements each complementary and capable of hybridization to a particular genomic DNA sequence. The nucleic acid target elements comprise any of genomic DNA nucleic acids, oligomer nucleic acids or cDNA nucleic acids complementary to expressed gene sequences, or a mixture of any of these.

In the preferred embodiment of the invention, the chromosomal DNA sample is separately labeled with a first detectable marker and is co-hybridized to the array with a reference nucleic acid, which is also labeled but with a different detectable marker. The reference nucleic acid can be from a normal tissue sample of the same type of tissue as that of the patient being tested, but preferably is total placental DNA sample. Preferably, the detectable markers are different fluorescent markers. The reference nucleic acid is chosen to permit assessment of the gene amplification or gene deletion status of the tissue sample relative to the reference. After a suitable hybridization time, the fluorescent color presence and intensity are detected at each target element of the array. Comparison of the fluorescent intensity ratios between fluorescent colors at a particular target element provides measurement of the copy number for genomic DNA sequences which are complementary to that target element. It is also preferred to use a microarray having a target element density of at least 50 different target elements in less than one square centimeter of the solid support surface.

The invention has the significant clinical advantage of guiding selection of expensive cancer adjuvant drugs for use with patients most likely to respond positively to the individual drug. For example, a genomic DNA microarray simultaneously measuring 59 separate gene amplifications in diseased tissue can be used to stratify solid tumor cancer patients, such as breast cancer patients, into at least nine groups based on the presence or absence of at least five different gene amplifications: those most likely to respond to (i) anti-Her-2/neu therapy (Herceptin®), (ii) anti-EGFR therapy (C225 antibody), (iii) anti-AKT1 therapy (cisplatin), (iv) anti-PIK3CA therapy, (v) anti-thymidylate synthase therapy (5-fluorouracil), (vi) anti-Topoisomerase II alpha therapy (anthracyclin, e.g. doxorubicin), (vii) anti-cmyc therapy, (viii) combination of anti-Her-2/neu therapy and anti-AKT1 therapy, and (ix) combination of anti-EGFR and anti-AKT1 therapy. The invention has the further advantage of identifying patients most likely to respond synergistically to a particular combination of adjuvant therapies.

The invention has yet another advantage, compared to use of nucleic acid microarrays measuring only gene expression changes in the diseased tissue from normal tissue, of measuring changes in a more stable analyte-chromosomal DNA, than the labile mRNA necessary for gene expression analysis. Moreover, the normal state of a gene locus in chromosomal DNA is always known: two, one on each of the two copies of a human chromosome (except for genes on the X and Y chromosomes in males, where the normal number is one.) Thus, abnormalities in chromosomal DNA are more readily determined than the measurement of changes in gene expression.

The invention has broad utility in human disease management by providing more complete genetic assessment data to guide therapy selection and in human and animal drug development programs by assessing therapeutic candidate effects. Particular cancers, which are characterized by gene amplification driving over-expression of the mRNA for the amplified gene, may be more aggressive diseases and need more aggressive therapies. The chromosomal DNA mechanism that drives over-expression is fundamental in understanding what therapeutic interventions may be appropriate. Thus, patient classification based on the characterization of both gene amplification and gene deletion by the methods of the invention can lead to improved cancer therapy.

BRIEF DESCRIPTION OF THE DRAWINGS

FIG. 1(a) depicts a microarray chip useful in the preferred embodiment of the invention.

FIG. 1(b) shows a probe clip useful in the preferred embodiment of the invention.

FIG. 1(c) shows a top view of a chip holder useful in the preferred embodiment of the invention.

FIG. 1(d) depicts a side view of the chip holder useful in the preferred embodiment of the invention.

FIG. 1(e) illustrates a completed hybridization chamber useful in the preferred embodiment of the invention.

DETAILED DESCRIPTION OF THE INVENTION

(1) Definitions

Figure 1A:
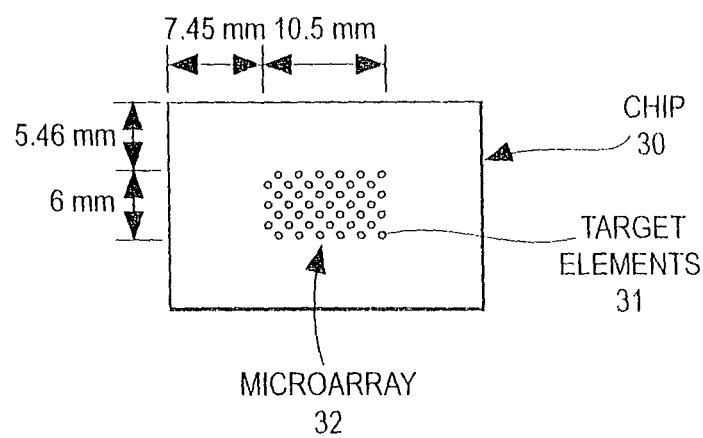
FIGS. 1(a) through 1(e) depict the components of a preferred hybridization cartridge for use in performing the inventive methods.
Figure 1B:
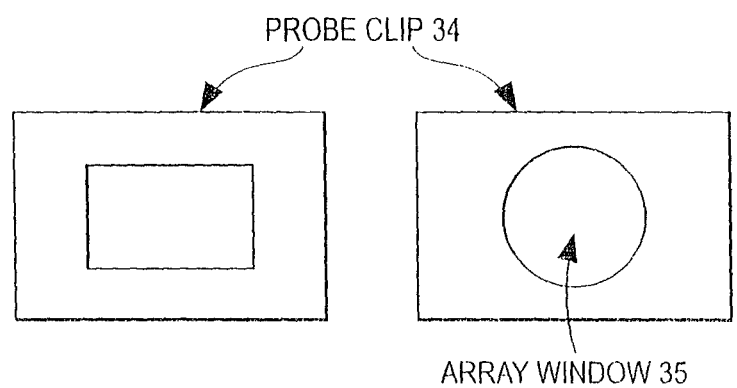

The following abbreviations are used herein:
bp—base pair
CGH—Comparative Genomic Hybridization
DAPI—4, 6 diamidino-2-phenylindole
dCTP—deoxycytosine triphosphate
DNA—deoxyribonucleic acid (in either single- or double-stranded form, including analogs that can function in a similar manner)
dUTP—deoxyuridine triphosphate
FISH—fluorescence in situ hybridization
kb—kilobase
mm—millimeter
mRNA—messenger RNA
ng—nanogram
nl—nanoliter
RNA—ribonucleic acid in either single- or double-stranded form, including analogs that can function in a similar manner
μg—microgram
μl—microliter
μm—micrometer
μM—micromole The term "nucleic acid" or "nucleic acid molecule" refer to a deoxyribonucleotide or ribonucleotide polymer in either single- or double-stranded form, including known analogs of natural nucleotides that can function in a similar manner as naturally occurring nucleotides.

The term "exon" refers to any segment of an interrupted gene that is represented in the mature mRNA product. Some protein coding genes do have exons that are non-coding, e.g., exon 1 of the human c-myc gene. Perhaps all protein coding genes have first and last exons that are partially coding.

The terms "single copy sequence" or "unique sequence" refer to a nucleic acid sequence that is typically present only once per haploid genome, such as the coding exon sequences of a gene.

The term "complexity" is used herein according to standard meaning of this term as established by Britten, et al., *Methods of Enzymol.*, 29:363 (1974). See also Cantor and Schimmel, *Biophysical Chemistry: Part III* at 1228-1230, for further explanation of nucleic acid complexity.

The term "target element" refers to a region of a substrate surface that contains immobilized or attached nucleic acids capable of hybridization to chromosomal nucleic acids isolated from a tissue sample.

"Bind(s) substantially" refers to complementary hybridization between a tissue nucleic acid and a target element nucleic acid and embraces minor mismatches that can be accommodated by reducing the stringency of the hybridization media to achieve the desired detection of the tissue polynucleotide sequence.

The terms "specific hybridization" or "specifically hybridizes with" refers to hybridization in which a tissue nucleic acid binds substantially to target element nucleic acid and does not bind substantially to other nucleic acids in the array under defined stringency conditions. One of skill will recognize that relaxing the stringency of the hybridizing conditions will allow sequence mismatches to be tolerated. The degree of mismatch tolerated can be controlled by suitable adjustment of the hybridization conditions.

One of skill will also recognize that the precise sequence of the particular nucleic acids described herein can be modified to a certain degree to produce tissue nucleic acid probes or target element nucleic acids that are "substantially identical" to others, and retain the ability to bind substantially to a complementary nucleic acid. Such modifications are specifically covered by reference to individual sequences herein. The term "substantial identity" of polynucleotide sequences means that a polynucleotide comprises a sequence that has at least 90% sequence identity, and more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is complementary to all or a portion of a reference polynucleotide sequence.

Sequence comparisons between two (or more) polynucleotides are typically performed by comparing sequences of the two sequences over a "comparison window" to identify and compare local regions of sequence similarity. A "comparison window," as used herein, refers to a segment of at least about 20 contiguous positions, usually about 50 to about 200, more usually about 100 to 150, in which a sequence may be compared to a reference sequence of the same number of contiguous positions after the two sequences are optimally aligned.

Optimal alignment of sequences for comparison may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U. S. A.*) 85:2444 (1988), and by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

Another indication that nucleotide sequences are substantially identical is if two molecules hybridize to the same sequence under stringent conditions. Stringent conditions are sequence dependent and will be different in different circumstances. Generally, stringent conditions are selected to be about 5° to about 25° C. lower than the thermal melting point (Tm) for the specific sequence at a defined ionic strength and pH. The Tm is the temperature (under defined ionic strength and pH) at which the strands of a DNA duplex or RNA-DNA hybrid are half dissociated or denatured.

As used herein, a "probe" is defined as a population or collection of tissue or reference chromosomal DNA molecules capable of binding to a target element comprising nucleic acid of complementary sequence through one or more types of chemical bonds, usually through hydrogen bond formation. The probe populations are directly or indirectly labeled as described below. The probe populations are typically of high complexity, for instance, being prepared from total genomic DNA isolated from a tissue cell or tissue cell population.

(2) Patient Stratification for Therapeutic Selection

The invention comprises a clinical diagnostic method for classifying human cancer patients into various groups eligible for specific forms of therapy, particularly adjuvant chemotherapy. After the stratification of a particular patient into a particular cancer therapy group through use of the invention, the physician can combine the stratification choice with other clinical information about the patient in the selection of therapy. For example, a physician can require additional tests, such as a single nucleotide polymorphism (SNP) assay for genetic variations in the patient that would impact the performance of a particular therapy. Multiple SNP assays and formats are available.

The invention thus comprises a method of cancer patient stratification into one of at least four cancer therapy groups comprising:

(a) providing a diseased tissue or suspected disease tissue sample from a patient;

(b) extracting chromosomal DNA from the tissue sample to produce a chromosomal DNA sample;

(c) hybridizing the chromosomal DNA sample to a nucleic acid microarray comprising (i) nucleic acid target elements attached to a solid support wherein the nucleic acid target elements comprise polynucleotide sequences substantially complementary under preselected hybridization conditions to human genomic chromosomal DNA and (ii) a sufficient number of nucleic acid target elements to detect a sufficient number of gene amplifications or gene deletions in the chromosomal DNA sample to permit patient stratification into one of at least four cancer therapy groups; and (d) stratifying the patient into one of at least four cancer therapy groups based on presence or absence of at least one chromosomal gene amplification or deletion.

The invention has significant clinical utility today because it can be used to identify patient that are most likely to respond to existing adjuvant cancer therapies. The Applicant believes that particularly effective adjuvant therapies are those targeted at genes which are over-expressed in the diseased tissue cells due to chromosomal gene amplification at the chromosome location of the gene. The method of the invention builds on this belief to stratify patient into treatment groups.

The molecular target, such as the expressed protein of a gene, for particular cancer adjuvant therapies is often known and the method of the invention identifies the amplification or deletion at the chromosome level of the location of the gene coding for the molecular target. For example, the Her-2/neu gene, the Topoisomerase II gene, the cmyc gene, the AKT1 gene, the EGFR (epidermal growth factor receptor) gene, the thymidylate synthase gene, the PIK3CA gene mapping to chromosome region 3q26, and the p53 tumor suppressor gene have all been identified as therapeutic targets. The following adjuvant cancer therapies are presently in clinical use, in clinical trials or described in the patent/scientific literature: (i) anti-Her-2/neu therapy (Herceptin® marketed by Genentech, South San Francisco, Calif.), (ii) anti-EGFR therapy (C225 antibody), (iii) anti-AKT1 therapy (cisplatin, see R. Dullea et al., "Induction of Apoptosis by CP 358,774, an Inhibitor of Epidermal Growth Factor (EGFR) Tyrosine Kinase, in Combination with Cisplatin (CDDP)", Abstract #2550, Proceedings of the 91st Annual Meeting of the American Association of Cancer Research, April 2000), (iv) anti-PIK3CA therapy, (v) anti-thymidylate synthase therapy (5-fluorouracil), (vi) anti-Topoisomerase II therapy (anthracyclin, eg. doxorubicin), (vii) anti-cmyc therapy (see E. McGuffie et al., "Inhibition of Colon Cancer Cell Growth by a Triple Helix-Forming Phosphorothioate Oligonucleotide Targeting the C-MYC Gene", Abstract #4081, Proceedings of the 91st Annual Meeting of the American Association of Cancer Research, April 2000), (viii) combination of anti-Her-2/neu therapy and anti-AKT1 therapy, and (ix) combination of anti-EGFR and anti-AKT1 therapy. For patients with tumors exhibiting p53 gene deletion, several therapies developed by Onyx Pharmaceuticals are in clinical trials for different cancers.

The methods of the invention permit classification of a patient into multiple treatment categories based upon chromosomal analysis. For example, a patient whose breast tumor exhibits gene amplification of the Her-2/neu gene and of the Topoisomerase II gene may show a synergistic response to treatment with a combination of Herceptin targeted at Her-2/neu with doxorubicin (or another anthracyclin) targeted at the Topoisomerase II alpha gene. Thus the invention can be used to show to the physician possibly synergistic adjuvant therapy combinations. In addition, as additional correlations between cancer therapies and chromosomal abnormalities are made, the patients can be classified into additional therapy groups with the methods of the invention.

The methods of the invention combine the capability of assessment of a large number of nucleic acids provided by microarray test formats with the multi-color, comparative hybridization power of CGH to assess simultaneously genomic abnormalities at multiple sites in the chromosomal DNA of the tissue sample. The methods of the invention employ hybridization under suitable hybridization conditions to a nucleic acid array comprising multiple nucleic acid target elements of a genomic chromosomal DNA derived from a tissue sample. The nucleic acid target elements comprise either genomic DNA, oligomer or cDNA nucleic acids complementary to expressed gene sequences, or a mixture of the two. A target element complementary to a particular expressed gene sequence is also complementary to the exon sequences of genomic DNA. Hence, a genomic DNA target element and a cDNA target element can each be used in an microarray format for hybridization to genomic DNA from a tissue sample. The nucleic acid populations are separately labeled with different detectable markers and comprise (1) a reference nucleic acid, which is representative of normal genomic chromosomal DNA in the tissue sample, and (2) a genomic chromosomal DNA, which is representative of the genomic status of the tissue sample. The labeled nucleic acid populations are co-hybridized to the array. Preferably, all of the nucleic acid populations applied to the array are each labeled with different fluorescent markers. The reference nucleic acid is chosen to permit assessment of the genomic state of the tissue sample relative to the reference. After a suitable hybridization time, the fluorescent color presence and intensity are detected at each target element of the array. Comparison of the fluorescent ratios between colors at a particular target element provides measurement of the copy number for genomic DNA sequences which are complementary to that target element.

The choice of genomic, cDNA or a mixture of target elements can vary with the tissue and analysis sought. For example, cDNA target elements are advantageous because the effect of repeat sequences present in some genomic DNAs is decreased and more precise detection of gene amplification or gene deletion is possible. Genomic DNA target elements are advantageous because the higher complexities (ie. longer sequences) can produce greater signal. A mixture of genomic DNA and cDNA target elements can also be used to provide more detailed genomic and expression analysis.

Preferably, the method uses the commercially available AmpliOnc I microarray and the GenoSensor Reader (both from Vysis, Inc., Downers Grove, Ill.) to perform the gene amplification and deletion analysis. The AmpliOnc I microarray comprises 59 different target elements, each replicated three times, for assessment of 59 different oncogenes for amplification or deletion in the patient specimen. Additional details on the AmpliOnc I and the GenoSensor Reader are available at www.vysis.com.

(3) Nucleic Acids in the Target Elements

The nucleic acid sequences of the target elements can comprise any type of nucleic acid or nucleic acid analog, including without limitation, RNA, DNA, peptide nucleic acids or mixtures thereof, and can be present as clones also comprising vector sequences or can be substantially pure. Arrays comprising peptide nucleic acids are disclosed in U.S. Pat. No. 5,821,060, "DNA Sequencing, Mapping and Diagnostic Procedures Using Hybridization Chips and Unlabeled DNA," H. Arlinghaus, et al.

The nucleic acids of a target element typically have their origin in a defined region of the human genome (for example a clone or several contiguous clones from a human genomic library), or correspond to a functional human gene, which may or may not be complete (for example a full or partial cDNA sequence). The target nucleic acids can also comprise inter-Alu or Degenerate Oligonucleotide Primer PCR products derived from cloned DNA.

The nucleic acids of a target element can, for example, contain specific genes or be from a chromosomal region suspected of being present at increased or decreased copy number in cells of interest, e.g., tumor cells. For example, separate target elements can comprise DNA complementary to each of the oncogene loci listed in Table 2 below. The target element may also contain an mRNA or cDNA derived from such mRNA, suspected of being transcribed at abnormal levels, for example, expressed genes mapping to the gene loci in Table 2 below.

Alternatively, a target element may comprise nucleic acids of unknown significance or location. An array of such elements could represent locations that sample, either continuously or at discrete points, any desired portion of a genome, including, but not limited to, the entire human genome, a single human chromosome, or a portion of a human chromosome. The number of target elements and the complexity of the nucleic acids in each would determine the density of analysis. For example, an array of 300 target elements, with each target containing DNA from a different genomic clone, could sample, i.e., analyze, the entire human genome at 10 megabase intervals. An array of 3,000 target elements, with each containing 100 kb of genomic DNA, could give substantially complete coverage at one megabase intervals of the unique sequence regions of the human genome. Similarly, an array of target elements comprising nucleic acids from anonymous cDNA clones or complementary to Expressed Sequence Tags ("ESTs") would permit identification of genomic DNA changes corresponding to expressed gene sequences that might be differently expressed in some cells of interest.

One of skill will recognize that each target element can comprise a mixture of target nucleic acids of different lengths and sequences. A target element will generally contain more than one copy of a cloned or synthesized piece of DNA, and each copy can be broken into fragments of different lengths. The length and complexity of the target element sequences of the invention is not critical to the invention. One of skill can adjust these factors to provide optimum hybridization and signal production for a given hybridization procedure, and to provide the required resolution among different genes or genomic locations.

The target elements can comprise oligomers, such as those in the range of 8 to about 100 bp, preferably 20 to 80 bp, and more preferably about 40 to about 60 bp, which can be readily synthesized using widely available synthesizer machines. Oligomers in target elements can also be synthesized in situ on the array substrate by any methods, such as those known in the art. The oligomer sequence information can be obtained from any convenient source, including nucleic acid sequence data banks, such as GENBANK, commercial databases such as LIFESEQ from Incyte Pharmaceuticals, Inc. (Palo Alto, Calif.), or EST data such as that produced by use of SAGE (serial analysis of gene expression). For oligomer or partial cDNA elements, one need only synthesize a partial sequence complementary to a part of the mRNA for the gene or complementary to an identifiable, critical sequence for the gene (critical in the sense of the sequences coding for the functional parts of the expressed protein, i.e., of the receptor binding site).

The target elements can comprise partial or full-length cDNA sequences, either synthesized for smaller cDNAs or cloned, preferably having a complexity in the range of about 100 bp to about 5,000 bp. cDNA target elements can be readily obtained from expressed gene sequence cDNA libraries from a desired tissue, which are produced using conventional methods or obtained from commercial sources, such as the libraries maintained by Genome Systems, Inc. (St. Louis, Mo.), Research Genetics (Huntsville, Ala.) and Clonetech (South San Francisco, Calif.).

The target elements can comprise genomic DNA sequences of any complexity, but generally of a complexity of about 20,000 bp to about 250,000 bp, and preferably about 50,000 bp to about 175,000 bp. Genomic DNA can be obtained from any mapped genomic clones produced by standard cloning procedures or obtained from commercial sources, such as the chromosome specific libraries maintained by the American Type Culture Collection (Rockville, Md.), hereinafter ATCC. A preferred genomic library source is the human DNA BAC library maintained by Genome Systems.

The identification of genomic DNA or cDNA selected for use in the target elements can be determined by the location of chromosomal sequences known or identified as amplified or deleted or of genes over- or under-expressed. The identification of genomic or cDNA clones is done by designing primer sequence pairs using, for example, genetic data in Gene Map '98 maintained by the U. S. National Institute of Health or the Genome Data Base. For example, the Her-2 gene is believed to comprise about 40 kb of genomic sequence and a PCR primer pair can be designed based upon the published Her-2 sequence. The PCR primer pair or the PCR amplicon product can then be used to screen a genomic DNA library to identify clones containing complementary sequences. The genomic DNA clones identified in the screen can be used on a microarray in the method of the invention to identify genomic abnormality at the Her-2 locus.

(4) Target Elements

The target elements can be of varying dimension, shape and area. The target elements can comprise physically separated spots produced by printing methods, for example, mechanical transfer, gravure, ink jet or imprint methods. The target elements also can be closely abutted such as those produced by the photolithographic in situ array synthesis of U.S. Pat. No. 5,445,934. The target elements are preferably generally round in shape on a planar surface. Generally, smaller elements are preferred, with a typical target element comprising less than 500 microns in diameter. Particularly preferred target element sizes are between about 5 microns and 250 microns in diameter to achieve high density.

The target element density can be any desired density and is preferably one typical of nucleic acid microarrays, i.e. greater than about 50 target elements per square centimeter. For the preferred use in human disease management, the target element density is preferably in the range of about 50 to about 10,000 target elements per square centimeter of substrate surface. Higher or lower densities can be desirable and higher densities can be preferred for use in drug development to permit examination of higher numbers of expressed gene sequences.

(5) Microarray Manufacture

The microarray can be manufactured in any desired manner and both robotic deposition and synthesis in situ methods for array manufacturing are known. See for example, U.S. Pat. Nos. 5,486,452, 5,830,645, 5,807,552, 5,800,992 and 5,445,934. It is preferred to manufacture the microarray using a robotic deposition method and apparatus, which employs robotic deposition of nucleic acids through a capillary needle or pin as disclosed in co-pending, commonly assigned U.S. patent application Ser. No. 09/085,625, filed May 27, 1998, "Improvements of Biological Assays for Analyte Detection," Muller, et al. (hereinafter "Muller, et al."), to produce a two dimensional microarray of physically separated or "spotted" target elements immobilized in rows and columns on a chromium coated-substrate.

A robotic applicator with multiple capillary needles can be used. A single needle applicator using a pin which is washed between applications of different nucleic acids, or using a robotic pin changer also can be used. The needle used is preferably a 33 gauge, one-inch long stainless steel capillary syringe needle. The needle is connected to a nucleic acid reservoir, preferably a Luer lock syringe tip. A preferred needle and reservoir is available commercially from EFD, (East Providence, R.I.). It is preferred to use multiple capillary needles, each depositing a different nucleic acid, thereby eliminating a washing step between depositions.

Any suitable amount of nucleic acid is deposited in each target element, with the target element size dependent on the amount deposited. For each target element, the amount can be from about 0.05 nl to about 5.0 nl of a nucleic acid solution of 1 µg/µl nucleic acid concentration. For a density of 1,000 target elements/cm$^2$, the individual amount deposited per target element is about 0.2 nl to about 2.0 nl of 1 µg/µl solution. The nucleic acid is provided in any solvent that will permit deposition of denatured nucleic acid. Preferably, the nucleic acid is provided in 100 mM NaOH at 1 µg/µl concentration.

To assist robotic manufacturing, automated tracking and labeling methods and apparatus can be used, for example, in delivering the correct nucleic acid for deposition at a particular target element. For example, bar coding or transponder labeling or tracking of capillary pins containing different nucleic acids are useful to assure delivery of the correct nucleic acid to the desired target element. The use of bar coding or transponder labeling also permits better computer control of the manufacturing process.

A microarray comprising both cDNA and genomic DNA target elements can be produced in any arrangement. For example, the cDNA elements can be located in one portion of the array or can be interspersed among the genomic DNA target elements. Although the regularity of a two dimensional array on a planar substrate surface is preferred to permit easy fluorescence detection and analysis, the array can be manufactured in any desired configuration.

Individual target elements can appear only once or can be replicated to provide statistical power to analysis of results. For arrays with densities under 3,000 target elements per cm$^2$, it is preferred to manufacture the array so that each target element is replicated three times on the array, to provide better calibration of the results. Applicants have determined that when using a microarray of less than one cm$^2$ of substrate surface area, the replicates can be placed adjacent each other or separated without material effect on the results.

Preferably, individual microarrays are manufactured on a large, substrate plate or wafer, which is scored using procedures well known in the semiconductor industry for breakup into individual chips. Chromium-coated glass plates or wafers are available commercially from Nanofilm (Westlake Village, Calif.) and can be scored using conventional procedures. Thus, multiple chips can be manufactured at once on the same wafer with one robotic applicator, and then separated into individual chips. Before printing, the wafers are preferably washed using, in order, distilled water, isopropanol, methanol and distilled water washes. Nitrogen is used to blow-off excess water and the rinsed wafers are dried.

The preferred Muller, et al. apparatus uses X-Y and Z axis controllers for the capillary pin applicator with application of a burst of low air pressure to deposit each nucleic acid. It is further preferred to use a suitable Z-axis controller on the apparatus of Muller, et al. to avoid contact of the capillary pin with the substrate surface. Positioning the pin above the surface, preferably about 100 µm above, permits better spot size regularity and use of lower air pressure.

When beginning printing, the plate or wafer is equilibrated to room temperature. The Z-axis height of each chip is then determined for use by the robot controller. Preferably, the printing starts with deposition of a 300µ diameter "marker" spot in one corner of each chip for alignment control. The nitrogen pressure is low, preferably about 1 psi or less, and is a pressure sufficient to deposit the particular nucleic acid given its viscosity and amount to be deposited. The nitrogen pulse length is generally about 10 milliseconds.

It is also preferred to include various control target elements such as, for example, target elements comprising: (1) total genomic DNA, (2) vector DNA, (3) a pooled mixture of genomic DNA or cDNA from each target element, (4) total RNA from a normal tissue, or (5) total genomic or cDNA from a tissue with known abnormalities.

The control target elements can also include a series of target elements each comprising a nucleic acid of known copy number for a particular genomic sequence. For example, genomic DNA extracted from cell lines with 1, 2, 3, 4 and 5 copies of the human X chromosomes can be used.

For quality control of the preferred robotic deposition manufacturing, it is preferred to image the produced arrays using a stereo microscope and a CCD camera. An image of each chip is captured and analyzed. Chips with missing, mis-sized or misshaped target elements are identified and marked.

When using cloned cDNA or cloned genomic DNA, the vector sequences can be removed before deposition with any suitable process or retained if they do not significantly interfere with the hybridization. For cloned genomic DNA and cDNA, it is preferred to not remove the vector sequences.

Any suitable substrate can be used, including those disclosed in U.S. Pat. Nos. 5,445,934 and 5,807,552. The substrate can be for example, without limitation, glass, plastics such as polystyrene, polyethylene, polycarbonate, polysulfone and polyester, metals such as chromium and copper, metal coated substrates and filters of any material. The substrate surface bearing the immobilized nucleic acids is preferably planar, but any desired surface can be used including, for example, a substrate having ridges or grooves to separate the array target elements. The nucleic acids can also be attached to beads, which are separately identifiable. The planar chromium-coated glass substrate of Muller, et al. is preferred.

The nucleic acids of the target elements can be attached to the substrate in any suitable manner that makes them available for hybridization, including covalent or non-covalent binding. The non-covalent attachment method of Muller, et al. is preferred.

(6) Tissue Nucleic Acids

The nucleic acid populations can be derived from any tissue source, including human, plant and animal tissue. The tissue sample comprises any tissue, including a newly obtained sample, a frozen sample, a biopsy sample, a blood sample, an amniocentesis sample, preserved tissue such as a paraffin-embedded fixed tissue sample (i.e., a tissue block), a rare cell or cells isolated from blood or other body fluid, or a cell culture. Thus, the tissue sample can comprise a whole blood sample, a skin sample, epithelial cells, soft tissue cells, fetal cells, amniocytes, lymphocytes, granulocytes, suspected tumor cells, organ tissue, blastomeres and polar bodies. The tissue to be tested can be derived from a micro-dissection process to produce a more homogeneous cell population. Paraffin fixed tissue is pre-treated with any suitable process to remove the wax, and a paraffin pretreatment kit is available commercially from Vysis, Inc. Any suitable amount of tissue can be used, including a single cell, such as a human blastomere cell to be tested during in vitro fertilization procedures. Where only one or a few cells are available, such as when testing human fetal cells separated from maternal blood samples, a nucleic acid amplification technique to amplify the amount of nucleic acid can be used.

The chromosomal DNA sample derived from the tissue is produced by any suitable nucleic acid separation or purification process. Nucleic acid separation methods for both genomic DNA and for messenger RNA are available commercially, such as the QIAmp® tissue kit for DNA isolation from Qiagen.

In general, where greater than about one million cells of tissue are available, the tissue chromosomal DNA can be extracted and used without amplification. If less than about one million cells are available, a nucleic acid amplification or concentration is preferably used. Preferably, such an amplification technique is PCR. Care and appropriate controls should be used with PCR to avoid or identify any artefacts introduced.

(7) Reference Nucleic Acids

The reference nucleic acid population is any suitable nucleic acid collection chosen to serve as a reference. For example, the reference population can be total human genomic DNA from normal tissue, total mRNA extracted from a normal sample of the tissue to be tested and converted to cDNA, or a synthetic or naturally-occurring mixture of chromosomal DNA. The reference also can include a "spiked," known amount of a particular genomic or cDNA sequence to enable control analysis.

(8) Labeling

The labels used can be any suitable non-radioactive marker detectable by any detection method. For example, the labels can be fluorescent molecules or can be proteins, haptens or enzymes. Also, "mass spec" labels, such as different isotopes of tin, can readily be detected after hybridization to the array by laser removal and mass spectrometry process, such as MALDI (matrix-assisted laser desorption-ionization). See Wu, et al., *Analytical Chemistry* 66, 1637 (1994) and Wu, et al., *Rapid Communications in Mass Spectrometry*, 7, 142 (1993). Preferably the labels are each fluorescent markers having sufficient spectral separation to be readily distinguished from each other without need of extensive "cross-talk" correction, such as fluorescein, Texas Red and 5- (and 6-)carboxytetramethyl rhodamine. An extensive list of fluorescent label compounds useful for attachment to nucleic acids appears in U.S. Pat. No. 5,491,224, "Direct Label Transaminated DNA Probe Compositions for Chromosome Identification and Methods for their Manufacture," Bittner, et al. Fluorescent compounds suitable for use are available commercially from Molecular Probes (Eugene, Oreg.). Indirect labels, such as biotin and phycoerythrin, that are fluorescently labeled after hybridization to the array by contact with a fluorescent protein, such as avidin labeled with fluorescein, also can be used.

The reference chromosomal DNA and the tissue chromosomal DNA populations are labeled in any suitable manner, such as by end labeling, nick translation or chemical transformation. It is preferred to use nick translation to label the chromosomal DNA in a suitable fluorescent color using a fluorescent dUTP or dCTP. Manufacture of suitable fluorescently labeled dCTP is disclosed in K. Cruickshank, Anal. Biochemistry, "Quantitation of Fluorescent Nucleotide Incorporation by Capillary Gel Electrophoresis and Laser Induced Fluorescent Detection," (in press), hereinafter referred to as "Cruickshank." Suitable nick translation kits are available commercially.

Preferably, for use of total human genomic DNA as the reference population, the labeling is done by a bisulfite-catalyzed transamination process as disclosed in U.S. Pat. No. 5,506,350, "Production of Chromosome Region Specific DNA Sequences and Transamination," Bittner, et al. Total human genomic DNA labeled by such a process is available commercially from Vysis, Inc. (Downers Grove, Ill.).

The labeling method used preferably results in a label content of each nucleic acid population of about 0.3 to about 6.0 mole percent labeled nucleotides when using direct attachment of fluorophores to the nucleic acids. The quantities of each labeled tissue nucleic acid and reference nucleic acid to be used are preferably in the range of about 100 ng to about 1 µg, preferably about 300 ng to about 425 ng.

(9) Array Hybridization

The tissue and reference nucleic acid populations are hybridized to the microarray under suitable hybridization conditions, i.e., stringency, for a time selected to permit detection of hybridization of single copy genomic sequences. The hybridization conditions include choice of buffer, denaturant, such as formamide, salt additives and accelerant. Hybridization buffers containing formamide and dextran sulfate at specified pH and salt conditions, such as LSI Hybridization Buffer (Vysis, Inc.), are available commercially. The buffer will preferably have a pH of about 6.8 to about 7.2, a salt content of about 1.5×SSC to about 2.5×SSC, and a formamide content of about 40-50%. Suitable conditions can include a temperature of about 40 to about 80 degrees centigrade for a time sufficient to detect signal over background for both genomic and expression of about 1 to about 72 hours, preferably 12-24 hours. Hybridization accelerators, such as dextran sulfate, or acceleration techniques can be used if desired. Adequate diffusion of the tissue and nucleic acid populations into contact with all target elements is necessary. This can be achieved by simple diffusion, or by accelerating diffusion or overcoming diffusion limitations using any suitable means including mechanical mixing, such as by rocking, or fluidic diffusion, such as by microfluidic pumping of the labeled populations in and out of a hybridization chamber containing the array. The post-hybridization wash is preferably at a stringency greater than that of the hybridization.

When using an array comprising human genomic DNA target elements, it is also preferable to add to the hybridization mix an excess of unlabeled human repeat sequence DNA, such as Cot1 DNA available from Life Technologies, Inc., to suppress the non-specific signal resulting from hybridization of labeled repeat sequences present in the tissue nucleic acid population or in a reference genomic DNA, if used. Use of unlabeled repeat sequence DNA is generally in amounts of about 0.02 to about 5.0 µg per 1 ng of total labeled genomic DNA (both tissue and reference), and preferably about 0.1 to 0.5 µg per 1 ng total labeled genomic DNA.

The hybridization can be performed in any suitable apparatus that will maintain the populations in contact with the array for a suitable time. For example, the labeled populations can be added to the array, covered with a cover slip and then incubated in an oven at the preselected temperature. Preferably, a cover slip designed to provide a desired hybridization volume between its bottom surface and the top of the array substrate is used. The labeled populations can be added to an array contained in a sealed cartridge apparatus, such as disclosed in European Patent Application 0 695 941 A1, "Method and Apparatus for Packaging a Chip," published 7 Feb. 1996, by microfluidic injection and circulation. The hybridization also can be carried out in a miniaturized hybridization and assay chip, such as that disclosed in PCT Patent Application WO 97/02357, "Integrated Nucleic Acid Diagnostic Device," published 23 Jan. 1997. Such miniaturized chips are referred to as manufactured on a mesoscale, i.e., manufactured having volumes for fluid pathways and reaction chambers measured in amounts of $10^{-8}$ and $10^{-8}$ liters or less.

FIGS. 1(a) through 1(e) show components of a preferred hybridization cartridge. FIG. 1(a) displays the first component, a chromium coated glass "chip" 30 containing the immobilized nucleic acid target elements 31 of the microarray 32. The microarray 32 is preferably located in the center of the chip 30, as shown. In a preferred format, the chip is 25.4 mm long×16.93 mm wide×0.7 mm thick; and the microarray covers a 10.5 mm long×6 mm wide area. Shown in FIG. 1(b), the second component is a "probe clip" 33, depicted with two alternate shapes, square and circular, for "array window" 34. The probe clip 33 can be made from any suitable material, preferably plastic. The array window 34 is of a clear material, and is located and sized to permit ready imaging of the microarray. The probe clip 33 forms a hybridization chamber and fits snuggly over the array as a retainer and protective cover. Preferably, the array window 34 is 1.27 mm in diameter, centrally located in a 25.4 mm long×16.76 mm wide probe clip 33.

Figure 1C:
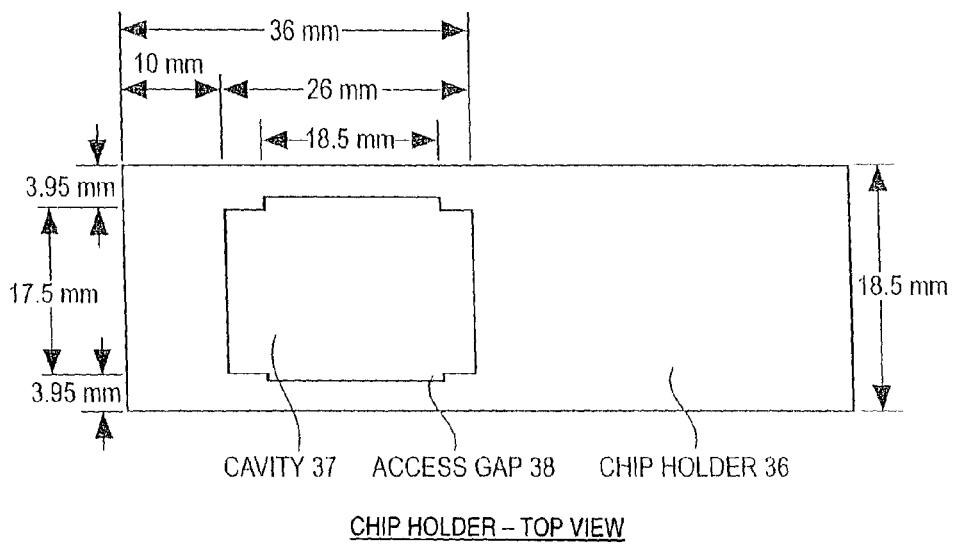
Figure 1D:
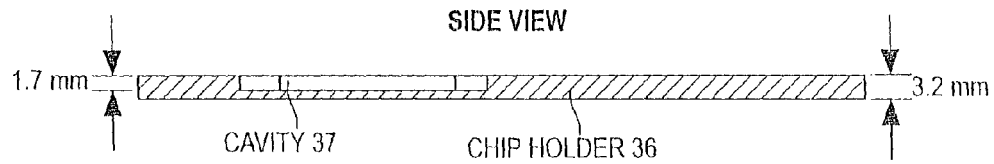

FIGS. 1(c) and 1(d) are top and side views of the fourth component, a chip holder 36, preferably made of a sturdy, injection moldable plastic, such as high-impact polystyrene, which is capable of withstanding necessary hybridization temperatures without loss of physical stability. The chip holder 36 can be of any desirable dimension for holding the chip, and preferably is 25.4 mm wide×76.2 mm long×3.2 mm thick. As shown, near one end, the chip holder 36 contains a cavity 37, preferably 26 mm long×18.5 mm wide×1.7 mm deep, sized to accept the chip 30 bearing the microarray 32. The cavity 37 along its length is also slightly wider, preferably 0.5 mm on each side, to create an access gap 38 to permit easier addition and removal of the probe clip and microscope cover slip. The surface of the cavity bottom is scored with shallow grooves to facilitate spreading of adhesive or fixative designed to hold the chip in place. The chip holder 36 at the end opposite the cavity 37 can be lightly scored across the width of the holder on its upper surface to provide a more grippable surface for the user. The chip holder bottom can be grooved to facilitate alignment in an array reader.

Figure 1E:
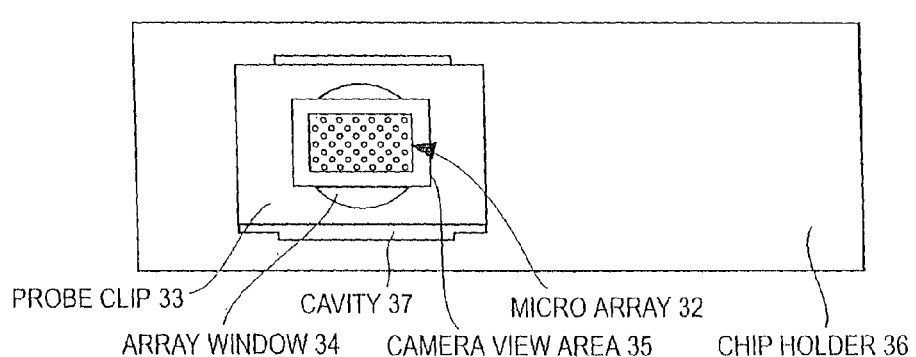

In manufacture of the completed cartridge, a microarray with desired target elements is manufactured as described above, and is then glued with any suitable adhesive into the bottom of cavity 37. The chip holder 36 bearing the array can then be shrink wrapped, and enclosed in a kit with the probe clip 33, a cover slip used in array imaging, and any other desirable reagents for labeling or extracting nucleic acids and/or performing the hybridization. To carry out the method of the invention, the user applies the hybridization solution comprising an appropriate buffer and the labeled nucleic acid populations (reference and tissue) to the surface of the microarray, and places the probe clip 33 on top of the microarray. The completed cartridge is depicted in FIG. 1(e). Also shown superimposed in FIG. 1(e) is the camera field of view 35 for the preferred imaging system of Che. The cartridge is then incubated in an oven, with desired humidity control at the desired hybridization temperature for the desired time.

When the hybridization is completed, the probe clip 33 is removed and the chip washed at a desired stringency, preferably in order with 2×SSC at room temperature for 5 minutes, with 2×SSC and 50% formamide at 40° C. for 30 minutes, and 2×SSC at room temperature for 10 minutes, to remove hybridized probe. Gel/Mount (Biomeda, Foster City, Calif.) and DAPI is applied to the array and a 18 mm×18 mm glass microscope cover slip is sealed over the array, still in holder 36. The covered chip is then imaged to detect the hybridization results.

(10) Array Detection

After hybridization, the fluorescence presence and intensity for each label color is detected and determined by any suitable detector or reader apparatus and method. Laser-based array scanning detectors are known to the art, see U.S. Pat. No. 5,578,832, "Method and Apparatus for Imaging a Sample on a Device," Trulsen, et al. Optical waveguide detection methods for array hybridization also have been disclosed, see U.S. Pat. No. 5,843,651, "Light Scattering Optical Waveguide Method for Detecting Specific Binding Events," D. Stimpson, et al. Preferably, a large field imaging apparatus and method, such as disclosed in co-pending, commonly assigned U.S. patent application Ser. No. 09/049, 798, "Large-Field Fluorescent Imaging Device," filed Mar. 27, 1998, D. Che, (herein Referred to as "Che"), and published as EP Application 99302384.5, filed Mar. 26, 1999, is used.

The large-field fluorescence imaging apparatus of Che uses reflective optics to couple the excitation beam generated by a high-power white light source onto the microarray surface to provide a high illumination intensity, and combines the high illumination intensity with the high detection efficiency of an array detector to provide a high image acquisition rate. The white light generated by the light source is collimated and filtered with a computer-controlled filter to provide the excitation beam. The excitation beam is passed through a field stop to form a well-defined beam pattern and then projected onto the array surface with a concave mirror. The concave mirror is disposed to image the field stop on the sample to define an illumination area which matches the field of view of the imaging optics. The fluorescent light generated in the sample is color filtered to reject scattered light of excitation color and imaged by the imaging optics onto the array detector to produce a fluorescent image of the sample.

The array imaging apparatus and method may employ digital image processing algorithms used in a programmed computer for data analysis, storage and display of digital image data from the imaging apparatus. Any suitable digital image processing, data storage and display software can be used for analysis of the array hybridization results. Digital imaging methods are known to those skilled in the art, for example, as disclosed in U.S. Pat. No. 5,665,549, "Comparative Genomic Hybridization," Kallionemi, et al., and U.S. Pat. No. 5,830,645.

The hybridization images are preferably captured and analyzed by use of a high resolution digital imaging camera, such as a SenSys 1600 Camera with PSI interface from Photometrics (Scottsdale, Ariz.), which receives the large field image directly from the detection optics. Any other suitable camera can also be used. The raw image data captured by the camera is stored in any suitable computer data base or data storage file. The raw image data is processed using suitable image analysis algorithms to determine the marker intensity at each target element of the microarray. Image analysis algorithms are well known to those skilled in the art, and a package of a large number of such algorithms is available as IPLab from Scanalytics (Fairfax, Va.)

Preferably, the image analysis algorithms carry out the following operations, implemented in appropriate computer software: (i) background correction, as necessary; (ii) array target element or "spot" segmentation for identification of individual array elements; (iii) spot grid assignment of a column and row number to each spot; (iv) spot data analysis, including verification of validity and presence of artifacts, averaging of data for replicate spots, normalization of data from all spots, and multi-experiment comparison and analysis; (v) single spot calculations, including the total intensity of each fluorescent marker color, the average DAPI counterstain intensity, the mean, mode, median and correlation coefficient of the per pixel ratios of fluorescent intensities, and the ratio of total tissue nucleic acid marker intensity to reference intensity, termed as the "mass ratio"; (vi) target summary analysis, including the number of valid replicates for a spot, the mean and coefficient of variation of the per spot mass ratios and the correlation coefficient of per pixel ratios across all spots. Preferably, the image analysis used standardizes the mean mass ratio such that the modal value is 1.00 using a window-based estimate of the mode.

The fluorescent data at each target element can be compared automatically to produce the ratio between any desired tissue and reference or between tissues. The image analysis also preferably comprises implementation of criteria set by the individual user for valid analyses, including (vii) exclusion of spots with pixels having saturated tissue or reference color channels; (viii) spot size and shape criteria for exclusion; and (ix) a "relation coefficient" exclusion for spots with relative coefficient values below threshold. The array data analysis can also include comparison algorithms to compare data from individual tests to data bases containing disease genotypes and phenotypes (i.e. listing of gene expression and chromosome abnormalities for particular diseases), which can identify possible diagnosis or choice of therapy based upon individual test results.

The image analysis preferably uses computer display and printing algorithms, such as those, for example, known to one of skill in the art, for computer monitor display and computer printing. The data display can include "pseudo-color" images selected by the user for the individual fluorescent colors of the tissue and reference nucleic acids. The array data display can be coupled with display of conventional chromosome ideograms to more clearly detail chromosome abnormalities identified in the practice of the method of the invention. See U.S. Pat. No. 5,665,549, FIG. 9, for an exemplary ideogram. Preferably, the array data is also displayed so that spots excluded from analysis are marked for ready identification by the user. This can be done by displaying that target element in an "error color" or with a colored circle around it.

In the preferred embodiment, the array reader and software automatically capture at least three images of each microarray after hybridization, specific for: (1) the DAPI counterstain (blue), (2) the tissue DNA (green), and (3) the reference DNA (orange). These images are referred to as color planes. However, images for more or different color planes can be taken. The image analysis portion of the software preferably uses one of the colors (preferably the DAPI image) to identify target elements and their location in the grid. Once all spots are identified the software analyses each pixel under each spot for its intensity in each of the remaining color planes. Suitable algorithms are employed to determine the local background for each of these color planes, which is then subtracted from the total intensity of each color. The background corrected intensities can then be averaged for all pixels under a particular target spot or group of spots, and this average intensity per pixel (e.g., A for DAPI intensity, B for tissue DNA intensity, C for reference intensity) can be used for various analyses.

For example, the intensity A may be used as an indicator of target spot quality, since the intensity of DAPI staining is a function of total amount of DNA attached at the target spot. Below a certain value for A (under controlled staining conditions) the amount of target element DNA may become rate limiting. The intensity C of the reference DNA can be used as an indicator for the efficiency of hybridization, since this reagent is preferably provided in a pre-determined concentration and is quality controlled.

In the preferred analysis, the most important information is the ratio of background corrected tissue intensity over background corrected reference intensity; i.e. for the above example the ratio of B/C. If more than one reference is used, then additional ratios can be taken to give informative data. These ratios can be determined for a group of spots, a single spot, or for each pixel under each spot.

In the most preferred mode, and for the example listed above, the B/C ratio is determined for each pixel, which should be independent on their absolute intensity in any of the colors. In other words, a plot of B versus C, for example, for each pixel under each spot should yield a scatter around a straight line, which should intersect both the X and Y axis at 0, if the background correction was appropriate. (Appropriate algorithms can generate such a plot by "clicking" on a given target spot or group of spots in the display.) This plot reveals two types of information:

First, the amount of scatter around the linear regression line is indicative of the quality of the data, and can be statistically evaluated to generate a correlation coefficient, which for ideal spots is 1 (i.e. all pixel values fall on the regression line). A value less than 1 indicates less than perfect data, and a value of 0.8 or less is preferably taken as an indicator that data from such a spot should be considered suspect. This scatter plot can be generated for a single spot or group of spots. Second, the slope of this regression line is the B/C intensity ratio for a given spot or group of spots.

In order to extract the desired biological information, the B/C ratio is preferably normalized with respect to a control spot or group of spots, for which these ratios can be correlated to a known level of DNA or RNA sequence in the test probe mixture. This is done as follows:

For analysis of genomic DNA the assumption is made that most of the tissue DNA sequences are in fact present in their normal copy number, i.e. two per genome (except for sequences from the sex chromosomes if the test tissue is from a male donor). For the reference DNA this is assumed to be true for all sequences (other than those from X or Y chromosomes if the reference DNA is from a male donor). Based on these assumptions the software compares the B/C ratio of all target spots and selects a group of ratios that appear to be very similar. This group of ratios is assumed to represent targets that are normal in the test tissue, and the average of that ratio is used to normalize all other ratios. In other words, the B/C ratios of all spots will be divided by the average B/C ratio, respectively, of this "normal group." Thus, the B/C ratio of all normal spots should be close to 1, while the B/C from targets that are aneuploid (present in copy numbers larger or smaller than 2), will be around 0.5 or less (gene deletions) or 1.5 or above (additions or gene amplifications).

The invention uses correlation of the reference normal gene copy number to the gene copy number of the patient tissue, by using the ratios described above as follows:

Assume that an assay was performed in which B is the intensity for the tissue genomic DNA, and C is the intensity for the reference genomic DNA. Then, the ratios to be obtained are as follows:

(B/C)=background corrected average pixel intensity ratio (Bg/Cg)=background corrected average pixel intensity ratio average for "normal" subgroup (B/C)/(Bg/Cg)=normalized B/C ratio=Bn/Cn The Bn/Cn ratio reveals the number of genomic copies of a given target sequence.

(11) Example Arrays

An example is a genomic DNA target element array containing genomic sequences for each of the 52 oncogene or amplified gene loci listed in Table 1.

TABLE 1

AmpliOnc Loci

| Gene or Chrom. Locus | Cyto. Location | Cancer Association |
|---|---|---|
| NRAS | 1p13.2 | Breast cell line |
| MYCL1 | 1p34.3 | Small cell lung cancer cell line, neuroblastoma cell line |
| FGR | 1p36.2-p36.1 | |
| LAMC2 | 1q25-q31 | Breast cell line |
| REL | 2p13-p12 | Non-Hodgkin's Lymphoma |
| ALK | 2p23 | lymphoma |
| MYCN (N-myc) | 2p24.3-q24.1 | Neuroblastoma |
| RAF1 | 3p25 | Non-small cell lung cancer |
| TERC (hTR) | 3q26 | Cervical, Head & Neck, Lung |
| PIK3CA | 3q26.3 | Ovarian |
| BCL6 | 3q27 | lymphoma |
| PDGFRA | 4q11-q12 | Giloblastoma |
| MYB | 6q22 | Colorectal; Leukemia; Melanoma |
| ESR1 (ER, ESR) | 6q25.1 | Breast |
| EGFR (ERBB1, ERBB) | 7p12.3-p12.1 | Glioma; Head & Neck |
| PGY1, MDR1 | 7q21 | Drug resistant cell lines |
| MET | 7q31 | Gastric |
| FGFR1, FLG | 8p11.2-p11.1 | Breast |
| MOS | 8q11 | Breast |
| ETO, MTG8, CBFA2T1 | 8q22 | leukemia |
| MYC (c-myc) | 8q24.12-q24.13 | Small cell lung, Breast, Esophageal, Cervical, Ovarian, Head & Neck, etc. |
| ABL1 (ABL) | 9q34.1 | CML |
| FGFR2 (BEK) | 10q26 | Breast |
| HRAS | 11p15.5 | Colorectal, Bladder |
| CCND1 (Cyclin D1, BCL1) | 11q13 | Head & Neck, Esophageal, Breast, Hepatic, Ovarian |
| FGF4 (HSTF1, HST) | 11q13 | Breast, Ovarian |
| FGFF3 (INT2) | 11q13 | Breast, Ovarian, Gastric, Melanoma, Head & Neck |
| EMS1 | 11q13 | Breast, Bladder |
| GARP(D11S833E) | 11q13.5-q14 | Breast |
| PAK1 | 11q13.5-q14 | Breast |
| MLL (ALL1) | 11q23 | leukemia |
| KRAS2 | 12p12.1 | Colorectal, Gastric, Adenocortical, Lung giant cell |
| CCND2 (Cyclin D2) | 12p13 | Lymphoma, CLL |
| TEL (ETV6) | 12p13 | leukemia |
| WNT1 (INT1) | 12q12-q13 | Retinoblastoma |
| SAS; CDK4 | 12q13-q14 | Sarcoma, glioma |
| GL1 | 12q13.2-q13.3 | Sarcoma, glioma |
| MDM2 | 12q14.3-q15 | Sarcoma, glioma |
| AKT1 | 14q32.3 | Gastric |
| PML | 15Q22 | leukemia |
| IGF1R | 15q25-q26 | rare amplicon |
| FES | 15q26.1 | rare amplicon |
| MRP | 16p13.1 | Drug resistant cell lines |
| MYH11 | 16p13.13-p13.12 | leukemia |

TABLE 1-continued

AmpliOnc Loci

| Gene or Chrom. Locus | Cyto. Location | Cancer Association |
|---|---|---|
| CBFB | 16q22 | leukemia |
| RARA | 17q12 | leukemia |
| HER-2/neu (EGFR2) | 17q12-21 | Breast, Ovarian, Gastric |
| TOPIIA | 17q21-q22 | Breast |
| YES1 | 18p11.3 | Gastric |
| BCL2-3' segment | 18q21.3 | Non-Hodgkin's Lymphoma |
| BCL2-5' segment | 18q21.3 | Non-Hodgkin's Lymphoma |
| INSR (insulin receptor) | 19p13.2 | Breast |
| JUNB | 19p13.2 | HeLa cell lines |
| CCNE (Cyclin E) | 19q12 | Gastric, Ovarian |
| BCL3 | 19q13 | lymphoma |
| AIB1 | 20q12 | Breast |
| CSE1L (CAS) | 20q13 | Breast |
| MYBL2 | 20q13.1 | Breast |
| PTPN1 | 20q13.1-q13.2 | Breast |
| ZNF217 (ZABC1) | 20q13.2 | Breast |
| STK15 (BTAK, aurora 2) | 20q13.2 | Breast, ovarian, colon, prostate, neuroblatoma and cervical |
| AML1 (CBFA2) | 21q22.3 | leukemia |
| BCR | 22q11.21 | leukemia |
| EWSR1 (EWS) | 22q12 | sarcoma |
| PDGFB (SIS) | 22q12.3-q13.1 | Rhabdomyosarcoma, liposarcoma |
| AR | Xq11.2-q12 | Prostate |

Note: Alternate names for a gene are shown in parentheses.

a Genomic DNA target elements derived from the clones listed in Table 1 contain human genomic DNA inserts of about 50 kb to about 200 kb in a PAC, P1 or BAC vector. This array is produced without separation of the vector sequences. Use of this array permits simultaneous identification of genomic amplification of each of these oncogene loci, as well as expression of the genes which map into these regions.

Yet another example is an array which contains genomic DNA from the oncogene loci of Table 1, supplemented by genomic DNA from the human tumor suppressor gene loci for: the p53, RB1, WT1, APC, NF1, NF2, VHL, MEN1, MENZA, DPC4, MSH2, MCH1, PMS1, PMS2, P57/KIP2, PTCH, BRCA1, BRCA2, P16/CDKN2, EXT1, EXT2, PTEN/MMAC1, ATM, and TP73 genes. The genomic DNA target elements are produced by selecting genomic DNA clones from a human genomic library that map to the loci for these tumor suppressor genes. This selection is done by the preparation of PCR primer pairs from the loci or genes and subsequent library screening to identify the clones. In this embodiment, the clones for the tumor suppressor loci can be about 20 kb to 250 kb, and are preferably about 50 kb to about 200 kb in complexity.

The preferred, commercially available AmpliOnc I microarray contains 59 different oncogene locations, including each of the 52 oncogene loci listed in Table 1 above.

(12) Utility of the Invention

The methods of the invention have significant utility in the fields of human disease management, human disease clinical research, human disease drug development and pharmacogenomics. In particular, by enabling more precise genetic detailing of suspected cancerous tissue, the invention will provide improved disease management through more tailored diagnosis and therapy selection.

The methods of the invention are particularly useful for genomic disease management of cancer. For example, the methods are useful for patient classification for any human cancer, including those of the breast, prostate, lung (small cell and non-small cell), ovary, cervix, kidney, head and neck, pancreas, testes, stomach, brain, soft tissue and skin, and of various blood or lymphatic system cancers such as leukemias and lymphomas. Once the tumor tissue genotype and phenotype are categorized by the method of the invention, the physician can combine this data with other clinical data to determine therapy and predict response to therapy.

EXAMPLE

The following example is intended to be merely illustrative of the invention and are not to be construed as limiting.

Example 1

(A) Procedures (i) Microdissected breast cancer tissue extracts were obtained from Dr. John Bartlett, Glasgow Royal Infirmary, University of Glasgow. These extracts were produced by first staining thawed, previously frozen breast cancer tissue sections with toluidine blue. Tumor/normal tissue was identified under a ×50 dissecting microscope, followed by microdissection with a scalpel blade into a microfuge tube. One sample (#10) was classified as normal tissue adjacent to tumor tissue (#9). The chromosomal DNA was extracted from the microdissected samples by addition of 25 microliters of proteinase K in TE buffer (pH 7.4) and incubation at 37 degrees C. for 48 hours. The proteinase K was then denatured by heading at 95 degrees C. for 20 minutes.

5 microliters of each 25 microliter of the proteinase K digested sample was amplified using DOP-PCR as described in Speicher, M. R. et al. (1993) Human Molecular Genetics 2, 1907-1914, using as a primer:

5'-CCG ACT CGA GNN NNN NAT GTG G-3'. (SEQ ID NO. 1)

1.5 microgram of each amplified sample was nick translated and labeled with Alexa-488 (Green) dUTP (Molecular Probes, Oregon). 1.5 microgram of genomic normal male reference DNA (Vysis, Inc., Downers Grove, Ill.) was amplified by DOP-PCR with the same procedure for the tumor extract, and was then nick translated and labeled with Alexa-594 (Red) dUTP (Molecular Probes, Oregon). The nick translated DNA's from the tumor and normal reference were precipitated in ethanol and the resulting pellet resuspended in purified water.

0.5 microgram of each the green-labeled tumor samples was combined with 0.5 microgram of the red-labeled male reference and Cot-1 DNA in hybridization buffer as described in the manufacturer's instructions for the AmpliOnc I assay. Each mixture was denatured according to the manufacturer's protocol and was then applied to the AmpliOnc I microarray (Vysis, Inc., Downers Grove, Ill.) and hybridized at 37 degrees C. for 18 hours. (The hybridization with the AmpliOnc I microarray was carried out in the apparatus of FIG. 1.) The microarrays were washed in formamide wash solutions at 40° C. The hybridized AmpliOnc I microarrays were then imaged and image captured using the GenoSensor Reader and the image data analysed using the GenoSensor software (both Vysis, Inc., Downers Grove, Ill.). The AmpliOnc I microarray contains the 31 human putative amplified gene loci are listed below, and were genomic human DNA inserted into BAC, PAC or PI cloning vectors. Each of the genomic DNA for these loci was produced with DNA of a single BAC, PAC or PI clone, although the individual insert sizes were not uniform. These BAC clones were obtained by screening the available genomic libraries with a primer sequence for each locus, as follows:

| GENE LOCUS | CLONE NO. | LIBRARY SOURCE[1] |
|---|---|---|
| MYCL1 | RMC01P052 | UCSF |
| FGR | RMC01P057 | UCSF |
| REL | BAC-274-P9 | GS |
| N-MYC | PAC-254-N16 | GS |
| RAF1 | BAC-98-L2 | GS |
| PIK3CA | PAC-97-B16 | GS |
| PDGFRA | BAC-619-M20 | GS |
| MYB | BAC-268-N4 | GS |
| EGFR | BAC-246-M20 | GS |
| MET | BAC-54-J7 | RG |
| FLG | BAC-566-K20 | GS |
| C-MYC | P1-469 | GS |
| ABL | PAC-763-A4 | RG |
| BEK | BAC-126-B28 | GS |
| HRAS1 | BAC-137-C7 | GS |
| BCL1 | PAC-128-18 | GS |
| INT2 | BAC-36-F16 | GS |
| KRAS | BAC-490-C21 | GS |
| WNT1 | BAC-400-H17 | GS |
| GLI | RMC12P001 | UCSF |
| CDK4 | BAC-561-N1 | GS |
| MDM2 | BAC-82-N15 | GS |
| AKT1 | BAC-466-A19 | GS |
| FES | P1I-2298 | GS |
| HER2 | P1-506 | GS |
| YES1 | BAC-8-P19 | GS |
| JUNB | BAC-104-C10 | GS |
| 20q13.2 | BAC-97 | GS |
| PDGFB | RMC22P003 | UCSF |
| AR | PAC-1097-P11 | RG |

[1]GS is Genome systems; RG is Research Genetics; UCSF is the LBL/UCSF Resource for Molecular Cytogenetics, University of California, San Francisco, Cancer Center. The clone number for each locus is shown. Human insert sizes ranged from about 60 kb to about 212 kb; not all inserts were measured. Chromosome location for each is in Table 2 above.

Results

Gene amplifications or gene deletions were detected as follows, with numbers showing relative level of gene amplification, with 1.0 being normal, ie. non-amplified:

factor beta) amplification was present in all patients who relapsed and died within 2 years and was present in only ⅓ of patients surviving for more than 8 years. None of the other amplifications detected showed an association with clinical outcome markers. It is also of interest that the "normal" tissue sample #10 in fact showed gene amplifications not present in the matched tumor sample #9, and also showed the Her-2 amplification characteristic. Based on the AmpliOnc I analysis, this "normal" tissue would likely not be classified as non-cancerous.

The results show that a microarray measuring multiple gene amplifications at the chromosomal level in a patient sample, can be used to stratify patients into particular cancer therapy groups. For example, future patients showing the Her-2 amplifications of patients #2 and #9 could thus be classified into possible anti-Her-2 therapy, such as treatment with Herceptin or with high dose anthracyclin. Patients such as patients #2, #4, #5, #7, #8 and #9 with PDGFB amplification which had poor clinical outcomes, could be eligible for more aggressive therapy and specifically for anti-PDGFB therapy. Patients like #4, #7 and #9, with AKT1 amplification could be eligible for cisplatin therapy targeted at AKT1. As additional gene specific therapies are developed, they can be more accurately selected based on the patient stratification achievable by microarray analysis for chromosomal gene amplification and gene deletion.

SEQUENCE LISTING (1) GENERAL INFORMATION
   (iii) NUMBER OF SEQUENCES: 1
(2) INFORMATION FOR SEQUENCE ID NO. 1:
   (i) SEQUENCE CHARACTERISTICS:
     (A) LENGTH: 22 base pairs
     (B) TYPE: nucleic acid
     (C) STRANDEDNESS: single
     (D) TOPOLOGY: linear
   (ii) MOLECULE TYPE: DNA (genomic)
   (xi) SEQUENCE DESCRIPTION: SEQ ID NO. 1:
CCG ACT CGA GNN NNN NAT GTG G 22

| Gene | #1 | #2 | #3 | #4 | #5 | #6 | #7 | #8 | #9 | #10 |
|---|---|---|---|---|---|---|---|---|---|---|
| FGR | | 2.85 | | | | | 2.85 | 1.77 | | |
| LAMC2 | | 1.33 | | 1.46 | | | | 1.65 | | |
| EGFR | | | 1.70 | 1.77 | | | | | 1.47 | Normal |
| MET | | | 0.66 | 0.65 | | | | 0.51 | | 0.61 |
| FGFR1 | | 1.52 | | | | | | 1.65 | | |
| HRAS | 1.36 | | | 1.57 | 1.52 | | 1.46 | | 1.52 | |
| CCND1 | 1.64 | | 1.33 | | | | 1.43 | 1.40 | | 1.31 |
| EMS1 | 1.42 | | 1.49 | 1.38 | | | 1.47 | | 1.35 | |
| FGF4/FGF3 | 1.39 | | 1.50 | 1.36 | | | 1.56 | | | |
| GARP | 2.41 | | 1.73 | | | | 2.03 | 1.78 | 1.52 | 1.57 |
| GLI | | | 1.64 | 1.45 | | | 1.36 | 1.47 | | |
| AKT1 | 1.67 | | 1.88 | | | | 2.54 | 1.78 | 1.68 | |
| MRP1 | 1.31 | 1.40 | 1.32 | | | | 1.75 | 1.37 | | 1.57 |
| ERBB2 (Her-2) | 4.43 | | | | | | | | 1.40 | 1.35 |
| TOP2A | 1.67 | | | | | | | | | |
| AIB1 | | | | | | | 1.98 | 1.53 | | 1.41 |
| BCR | 1.37 | | | 1.68 | 1.35 | | 1.87 | 1.79 | 1.77 | |
| PDGFB | | 1.68 | 1.57 | 1.74 | 1.58 | | 3.31 | 2.31 | 1.51 | 1.74 |

No correlation between nodal status or estrogen receptor status was observed with any of the above changes. However, Her-2 gene amplification was not present in any patient who survived more than 8 years, and in both cases above, the patient died within 2 veers. PDGFB (platelet derived growth The specification of this application is not intended to be limiting as to the scope of the invention. All patents, patent applications and published references cited herein are hereby incorporated by reference. The scope of the invention is determined by the following claims, including any and all equivalents thereof.

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (11)..(16)
<223> OTHER INFORMATION: a, c, g, t/u, unknown, or other

<400> SEQUENCE: 1
ccgactcgag nnnnnnatgt gg                                            22
```

I claim:

1. A method of cancer patient stratification into one of at least four cancer therapy groups comprising:
   (a) providing a diseased tissue or suspected disease tissue sample from a patient;
   (b) extracting chromosomal DNA from the tissue sample to produce a chromosomal DNA sample;
   (c) co-hybridizing the chromosomal DNA sample, labeled with a first fluorescent marker, and a reference DNA sample, labeled with a second fluorescent marker, to a nucleic acid microarray, said microarray comprising: nucleic acid target elements from EGFR, AKT1, HER-2/neu, and TOPIIA attached to a solid support, wherein the nucleic acid target elements comprise polynucleotide sequences substantially complementary under preselected hybridization conditions to human genomic chromosomal DNA and wherein there is a sufficient number of said nucleic acid target elements to detect gene amplifications of EGFR, AKT1, HER-2/neu, and TOPIIA in the chromosomal DNA sample;
   (d) comparing a fluorescent ratio between colors of the first and second markers at a particular nucleic acid target element to provide a measurement of a copy number for genomic DNA sequences which are complementary to that nucleic acid target element;
   (e) stratifying the patient into one of the at least four cancer therapy groups selected from the group consisting of anti-HER-2/neu therapy, anti-EGFR therapy, anti-AKT1 therapy, anti-Topoisomerase II therapy, combination of anti-HER-2/neu therapy and anti-AKT1 therapy, and combination of anti-EGFR and anti-AKT1 therapy, based on presence or absence in at least one chromosomal gene amplification; and
   (f) performing a cancer therapy based on (e).

2. The method of claim 1, wherein the tissue sample comprises at least one cell identified in or separated from a blood sample from a patient.

3. The method of claim 1, wherein the tissue sample comprises a microdissected solid tumor sample.

4. The method of claim 1, wherein the tissue sample comprises a blood sample.

5. The method of claim 1, wherein the tissue sample comprises a sputum sample.

6. The method of claim 1, wherein the tissue sample comprises a cervical Pap smear.

7. The method of claim 1, wherein the tissue sample comprises at least one cell identified in or separated from a urine sample from the patient.

8. The method of claim 1, wherein the target elements of the microarray comprise oligomers of a complexity of at least 50 base pairs in length.

9. The method of claim 1, wherein target elements of the microarray comprise polynucleotides of at least 30 kb.

10. The method of claim 1, wherein target elements of the microarray comprise polynucleotides of a complexity in the range of 50,000 base pairs to 175,000 base pairs.

11. The method of claim 1, wherein target elements of the microarray comprise cDNA polynucleotides of at least 500 base pairs in length.

12. The method of claim 1, further comprising sub-stratifying each patient into cancer therapy response groups based on single nucleotide polymorphism status of the individual.

13. The method of claim 1 wherein the microarray comprises target elements at a density in the range of 50 to 10,000 target elements per square centimeter of solid support surface.

14. The method of claim 1 further comprising processing data from the hybridization in step (b) in a programmed computer, storing raw and processed data in a database and displaying raw and processed data.

15. The method of claim 1 wherein the tissue sample comprises one cell.

16. The method of claim 1 wherein the target nucleic acid elements comprise at least one peptide nucleic acid.

17. The method of claim 1 wherein step (b) is performed in a mesoscale device.

18. The method of claim 1 wherein the chromosomal DNA sample is produced by a method comprising polymerase chain reaction.

19. The method of claim 14 which further comprises displaying at least one chromosome ideogram with the microarray data.

20. The method of claim 1 wherein the chromosomal DNA sample is produced by Degenerate Oligonucleotide Priming-Polymerase Chain Reaction.

21. The method of claim 1, wherein the patient is stratified into:
   (i) an anti-HER-2/neu therapy group based on presence of HER-2/neu gene amplification as indicated by the fluorescent ratio;
   (ii) an anti-EGFR therapy group based on presence of EGFR gene amplification as indicated by the fluorescent ratio;
   (iii) an anti-AKT1 therapy group based on presence of AKT1 gene amplification as indicated by the fluorescent ratio; and/or (iv) an anti-Topoisomerase II therapy group based on presence of TOPOIIA gene amplification as indicated by the fluorescent ratio.

\* \* \* \* \*